United States Patent [19]

Woods et al.

[11] 4,204,077

[45] May 20, 1980

[54] ETHERIFICATION PROCESSING OF LIGHT HYDROCARBONS

[75] Inventors: Hanbury J. Woods, Campbellville; John D. Chase, Oakville; Buenaventura B. Galvez, Islington, all of Canada

[73] Assignee: Gulf Canada Limited, Toronto, Canada

[21] Appl. No.: 948,072

[22] Filed: Oct. 2, 1978

[51] Int. Cl.² ............... C07C 41/00; C07C 41/10; C07C 41/12
[52] U.S. Cl. .................................. 568/697; 568/699
[58] Field of Search .................. 568/697, 918, 699

[56] References Cited

U.S. PATENT DOCUMENTS

| | | | |
|---|---|---|---|
| 2,571,151 | 10/1951 | McGrath et al. | 265/450 |
| 2,580,750 | 1/1952 | Fleming | 260/450 |
| 2,671,104 | 3/1954 | Grahame et al. | 260/450 |
| 3,213,593 | 10/1965 | Hendrix | 260/676 H X |
| 3,388,046 | 6/1968 | Hendrix | 568/918 |
| 3,482,952 | 12/1969 | Sieg et al. | 44/77 X |
| 3,726,942 | 11/1973 | Louder | 260/683.61 |
| 3,912,463 | 10/1975 | Kozlowski et al. | 568/697 |
| 4,118,425 | 10/1978 | Herbstman | 568/697 |

*Primary Examiner*—Howard T. Mars
*Attorney, Agent, or Firm*—D. R. Morrison

[57] ABSTRACT

In the processing of olefinic hydrocarbon mixtures containing isobutylene and isoamylene which are etherified with methanol to obtain higher octane components, unreacted methanol is removed from the etherified mixture by contact with a separate liquid glycol phase before unreacted hydrocarbons, substantially free of methanol, are distilled from the etherified mixture for further catalytic processing in which methanol is deleterious to the catalyst.

10 Claims, 1 Drawing Figure

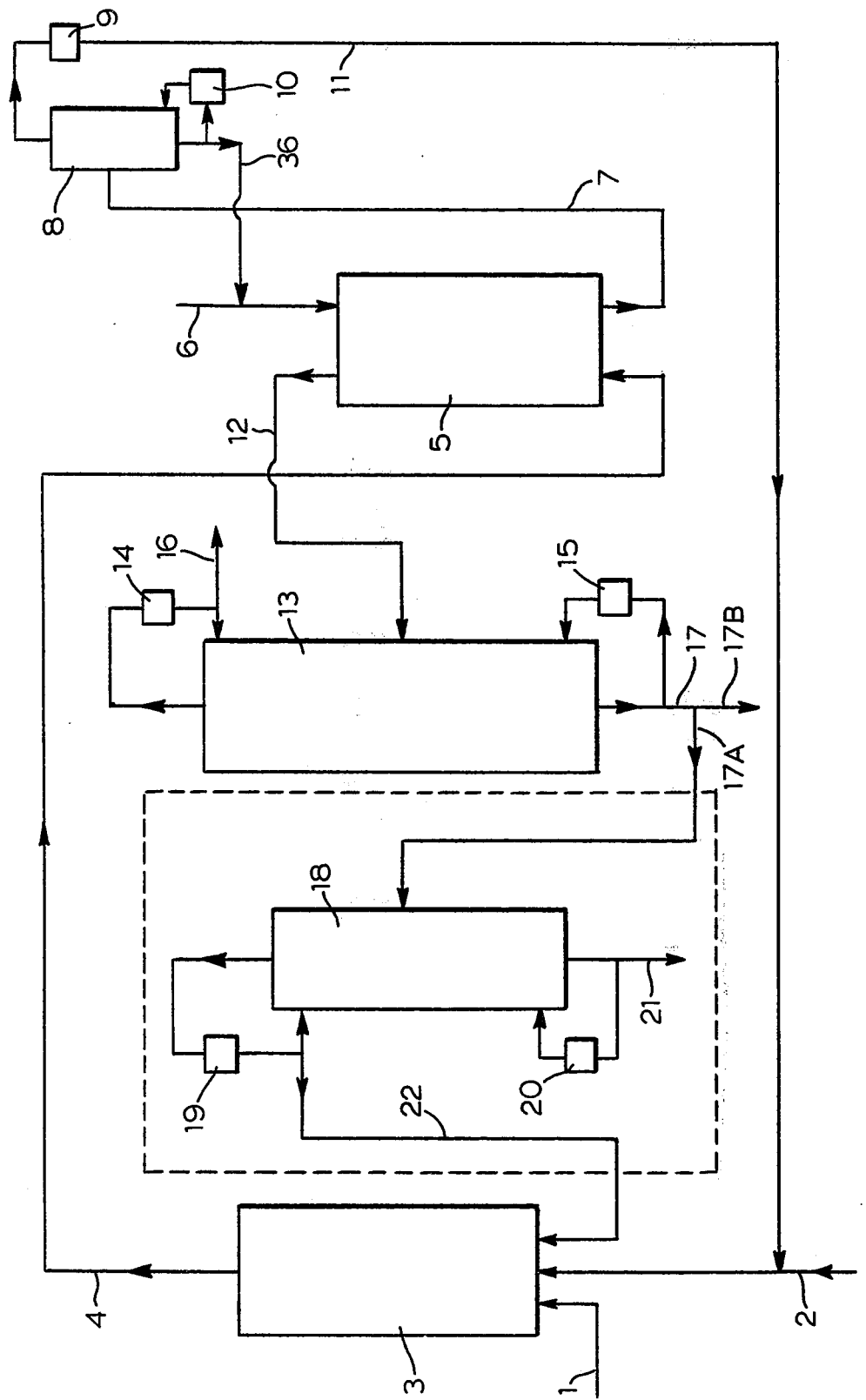

ETHERIFICATION PROCESSING OF LIGHT HYDROCARBONS

This invention relates to improvements in the processing of light olefinic hydrocarbon streams containing tertiary olefins and more particularly to processing in which the tertiary olefins in such streams are subjected to etherification and the remaining hydrocarbons in the streams are subsequently to be subjected to additional processing to produce high octane components suitable for blending into gasoline.

It is known in the art that olefinic mixtures of light hydrocarbons of predominantly four carbon atoms each can be processed to provide high octane gasoline ingredients by etherifying the isobutylene component thereof with methanol to convert the isobutylene to methyl tertiarybutyl ether (MTBE), a high octane ingredient for gasoline blending, and optionally further processing the remaining hydrocarbons of the mixtures to convert other components thereof to compounds of higher octane value, for example by polymerization or alkylation processes for making polygas and alkylate respectively. It is also known in the art that olefinic mixtures of hydrocarbons containing predominantly five carbon atoms each can be processed to convert most of the isoamylene content thereof to tertiaryamyl methyl ether (TAME) which is another high octane ingredient suitable for blending into gasoline. It has further been suggested in the art that olefinic mixtures containing hydrocarbons of both four and five carbon atoms each can be processed in an etherification reactor to convert simultaneously both four and five carbon atom tertiary olefins therein to the tertiary ethers MTBE and TAME. U.S. Pat. No. 3,482,952 suggests etherification of an even more complex olefinic mixture of hydrocarbons with from four to six carbon atoms inclusive, to form tertiary ethers of higher octane rating than the original hydrocarbon fraction, distillation to separate a higher boiling ether containing portion from the remaining hydrocarbons, and alkylation of the portion of remaining hydrocarbons to form a higher octane alkylated ingredient suitable for gasoline.

Because the etherification reaction between tertiary olefins and methanol is an equilibrium reaction, it is not possible to reduce the concentration of methanol in the effluent from the etherification process below the equilibrium concentration of methanol and ether products. Thus such effluent always contains some methanol. It is now known that such methanol, on distillation of the effluent, forms minimum boiling binary azeotropes, not only with the ethers MTBE and TAME and a number of the higher boiling hydrocarbons in the $C_5$-$C_6$ range, but also even with n-butane. Thus any attempt to fractionate, simply by distillation, the effluent of a process etherifying a mixture of $C_4$-$C_6$ hydrocarbons with methanol, is bound to produce a distillate containing some methanol; even a distillate free of binary ether-methanol azeotropes from such effluent contains some methanol-n-butane azeotrope (and some methanol-pentane azeotrope if $C_5$ hydrocarbons are taken into the distillate). Because methanol is so deleterious to the catalysts usually used in alkylation processes or in the polymerization process for production of polygas, it is not practicable to use, in such processes, the effluent from the etherification process in which an olefinic $C_4$-$C_6$ hydrocarbon fraction is etherified with methanol, even if the effluent is distilled to separate higher boiling material, notably the ethers, from the hydrocarbon material to be further processed by alkylation or polymerization.

The art of preparing the ethers MTBE and TAME from olefinic mixtures of hydrocarbons also has indicated a preference for separately etherifying olefinic mixtures of hydrocarbons of predominantly four carbon atoms each and olefinic mixtures of hydrocarbons of predominantly five carbon atoms each rather than etherifying them in admixture, in significant part because of the difficulty of separating, from the effluent of a process for their combined etherification, hydrocarbon streams of sufficiently low methanol content to be suitable for subsequent processing by alkylation or polymerization. It has now been found that, by means of a combination of either an absorption or an extraction step and one or more simple fractional distillation steps, it is possible to separate the effluent from an etherification process, in which an olefinic mixture of hydrocarbons containing predominantly both four and five carbon atom compounds is etherified with methanol, to provide a fraction containing substantially all of the ethers and at least one other fraction containing hydrocarbons substantially free of methanol and suitable for further processing, for example, by alkylation, polymerization to polygas, or other process in which methanol is deleterious to operation. Such alkylation, polymerization and other processes regularly require feeds containing less than 200 mole ppm of methanol, preferably less than 50 mole ppm and most preferrably less than 10 mole ppm of methanol.

The present invention thus consists in a method for processing an olefinic hydrocarbon stream, consisting essentially of a mixture including both four and five carbon atom etherifiable olefins, for the formation of high octane components for blending into gasoline, said method comprising 1. passing said stream into an etherification reactor with a proportion of methanol under etherifying conditions, to contact an etherification catalyst therein and etherify tertiary olefins in said stream, 2. passing the entire effluent stream from said etherification reactor into a glycol contacting unit and contacting it therein with a stream of liquid glycol to remove methanol from said effluent and reduce the methanol concentration in the effluent stream to no greater than 200 mole ppm in said effluent, 3. separating said effluent stream from said glycol and fractionally distilling the reduced effluent to separate a distillate containing hydrocarbons of predominantly four carbon atoms each and no greater than 200 mole ppm methanol from a higher boiling high octane fraction containing ethers and hydrocarbons of predominantly more than four carbon atoms each. The invention further consists in a process as aforesaid and including the additional step of fractionally distilling a proportion of said higher boiling fraction to separate a distillate of hydrocarbons of predominantly five carbon atoms each from a higher boiling ether containing portion, and recycling said distillate of hydrocarbons of predominantly five carbon atoms each as additional feed to said etherification reactor. The invention still further consists in a process as aforesaid and including the additional steps of fractionally distilling the glycol separated from the effluent stream to obtain a distillate of methanol and a residue of glycol, recycling said distillate of methanol as part of the methanol feed to said etherification reactor and recycling said residue of glycol to said glycol contacting unit as the stream of liquid glycol.

The invention may be more readily understood from the following description of the accompanying drawing which shows in diagrammatical form a flow sheet illustrating optional embodiments of the process of the invention. In accordance with the invention an olefinic stream of mixed hydrocarbons containing substantially only hydrocarbons of four and five carbon atoms each is supplied by a feed line 1 into an etherification reactor 3; a second feed line 2 feeds a stream of methanol to the reactor. In the reactor the methanol and hydrocarbons contact an etherification catalyst under etherifying conditions, thereby converting a large proportion of the tertiary olefins of the mixed hydrocarbon stream to tertiary ethers. The mixed stream of ethers and unreacted methanol and hydrocarbons flows from the reactor through line 4 into a counter-current extractor 5 where it contacts a stream of ethylene glycol from recycle line 36 or added to the extractor via line 6. In the extractor, unreacted methanol is extracted from the ether-hydrocarbon stream into the ethylene glycol stream. The ethylene glycol stream containing methanol is withdrawn from the extractor by line 7 and passes to a fractional distillation column 8, conveniently equipped with a condenser 9 and reboiler 10. The distillation column separates the methanol, which is withdrawn at the top of the column and is returned by line 11 as part of the methanol feed to reactor 3, from ethylene glycol which is withdrawn at the bottom of the column by line 36 for recycle to the extractor 5. The mixed ether-hydrocarbon stream, substantially completely freed of methanol, is withdrawn from the extractor 5 by line 12 and passed to a fractional distillation column 13 equipped with a condenser 14 and reboiler 15. In the distillation column 13 the lower boiling hydrocarbons containing predominantly four carbon atoms each are separated and withdrawn as a distillate stream from the top of the column via line 16. This stream of mixed hydrocarbons containing predominantly four carbon atoms each, being substantially completely free of methanol, is suitable for feeding directly to an alkylation unit or to a polygas unit for production of alkylate or polygas fractions to blend into gasoline. From the bottom of column 13 a residue stream 17, containing ethers produced in reactor 3 and hydrocarbons of predominantly more than four carbon atoms each, can be withdrawn via line 17B and passed directly to gasoline blending, for which it is a high octane component and eminently suited. This residue stream 17 from the bottom of column 13 contains substantially all the ethers formed from the tertiary hydrocarbons (both isobutylene and isoamylene) in the olefinic mixture of hydrocarbons originally fed to the etherification reactor; it additionally contains hydrocarbons of predominantly five carbon atoms each, including some isoamylene which passed unreacted through the etherification reactor, and usually some six carbon hydrocarbons. As an optional feature of this invention, part of this initially unreacted isoamylene is recycled to the etherification reactor by separating a proportion of the residue stream 17 and passing it via line 17A for additional processing illustrated in the part of the drawing enclosed by the dotted rectangle. The proportion of residue stream to be additionally processed is fed by line 17A to a fractional distillation column 18 equipped with a condenser 19 and a reboiler 20. This column is operated to separate the ethers and the higher boiling part of the hydrocarbons through the bottom of the column via line 21 and the more volatile predominantly five carbon atom hydrocarbons, including the isoamylenes, which distill through the top of the column, via line 22. Line 22 conducts this more volatile fraction back to reactor 3 where the isoamylenes in the fraction are again subject to etherification along with the hydrocarbon feed stream from line 1. The proportion of the residue stream 17 from column 13 which is passed through line 17A for recycle processing can vary between zero and 100 percent of the stream. When none of the stream is taken, the process of the invention achieves only single pass conversion to TAME of the isoamylenes in the feed which, with the excellent single pass conversion of isobutylene to MTBE that can be achieved, may be sufficient to provide the desired octane improvement of the feed stream, particularly in combination with the additional octane improvement that can be obtained by the alkylation or other treatment of the stream of hydrocarbons of predominantly four carbon atoms recovered from line 16. When 100% of the residue stream 17 from column 13 is directed through line 17A, the ether containing residue from the bottom of column 13 is all subjected to a fractional distillation which requires significant quantities of heat, the cost of which may not be warranted for the incremental increase in octane which is achieved by such a high degree of recycling. It is more expedient therefore to recycle considerably less than the total amount of the residue stream 17 from column 13, and a preferred proportion for recycle through line 17A is between 10% and 85% of the residue stream 17 and more preferrably between 15% and 40% of said stream. When a recycle portion is withdrawn through line 17A and fractionally distilled in column 18, the higher boiling, ether containing bottom fraction withdrawn through line 21 is a superior octane component for gasoline blending.

The glycol contacting unit for removal of methanol from the effluent stream of the etherification reactor, as referred to above, may be either a liquid-liquid type or a vapor absorber type, but preferrably is of the liquid-liquid type, most preferrably the counter-current liquid-liquid type. The vapor absorber type of contacting unit requires that the etherification reactor effluent all be vaporized before passing to the contacting unit, which increases the removal costs, therefore liquid-liquid extraction units are preferred, as they are generally at least as efficient as the vapor absorber type of contacting unit. The liquid glycol stream which is used to contact the reactor effluent stream for extraction of methanol therefrom can be a single liquid glycol or a mixture of liquid glycols, for example ethylene glycol, diethylene glycol, triethylene glycol, propylene glycol, and mixtures of any of these. The essential property of the liquid glycol in the extraction unit is its ability, as a separate phase, to absorb or extract substantially all of the methanol from the effluent and leave substantially all the dialkyl ethers in admixture with the hydrocarbons of the effluent for blending into gasoline. The simple (mono)ethylene glycol is the best and most preferred, as it combines optimum properties of extractant for methanol and low miscibility with MTBE and TAME. Di- and triethylene glycols are operable but less preferred because of lower solubility for methanol and increased miscibility with MTBE and TAME.

The temperature at which the methanol removal unit is operated generally is lower when using liquid-liquid extraction than when using a gas absorber type of unit. In either case it generally is in the range from 10° F. (−12° C.) to 450° F. (232° C.) and with the preferred liquid-liquid extraction units it is preferably in the range from 50° F. to 150° F. (10° C. to 65° C.). The mole flow rate of glycol, in proportion to the mole flow rate of effluent in the contacting unit, may be in the range from 0.10 to 4.0; preferably it is in the range from 0.20 to 0.70.

Conventional commercial equipment for conventional gas absorption or liquid-liquid extraction operations is suitable for the methanol removal unit required in the present invention. In particular, both packed and plate type vapor-liquid contacting columns are suitable for gas absorption if desired, and likewise either type of column can be used for liquid-liquid extraction. Additionally, other types of mechanical liquid-liquid contactors e.g. rotating disk contactors, can be used. Both counter-current and co-current liquid-liquid extractors are suitable, with the more efficient counter-current type being preferred.

The invention may be more readily understood from the following specific examples thereof which are given for illustration only and not to limit the following claims. The proportions given therein and throughout the specification and claims are proportions by weight unless otherwise specifically indicated.

EXAMPLE 1

An olefinic mixed hydrocarbon stream of hydrocarbons of predominantly four and five carbon atoms was separated from the products of a catalytic cracking operation, principally by fractional distillation; chromatographic analysis of the stream established that its composition was made up of 53.5% of four carbon atom hydrocarbons including 7.5% $C_4$ reactable with methanol to form ether (i.e. isobutylene) and 46.0% unreactable $C_4$'s, 39.5% of five carbon atom hydrocarbons including 16.7% $C_5$'s reactable with methanol to form ether (i.e. isoamylenes) and 22.8% unreactable $C_5$'s, and 7% of six carbon atom hydrocarbons (considered unreactable). This stream was fed continuously, together with a stream of methanol, into a tubular reactor packed with "Ionac C-252" (Trademark) commercial ion exchange resin in the acid form, used as an etherification catalyst; the molar ratio of methanol to total reactable $C_4$ and $C_5$ hydrocarbons in the reactor feed was maintained at 1.30. The total flow of feed to the reactor provided a liquid hourly space velocity in the reactor of 2.5. Pressure in the reactor was maintained around 13.6 atmospheres and temperature of the feed to the reactor at 160° F. (71° C.). Average temperature across the reactor during the exothermic reaction therein was 184° F. (84° C.). The etherification reactor effluent contained 6.5% methanol, which could not be adequately separated from the other components of the effluent by fractional distillation. The effluent was fed continuously, at a rate of 5.3 lb. moles per hour, to the bottom of a continuous counter-current packed bed extraction column, 2 inches (5 cm) in diameter and 14 feet (4.3 m) high, maintained at a pressure of 3.8 atmospheres. A counter-current stream of ethylene glycol at a temperature of 72° F. (22° C.) was fed to the top of the extraction column at a mole ratio of 0.45 in proportion to the feed to the bottom of the column. Extracted effluent (raffinate), withdrawn from the top of the column, was found to contain 10 mole ppm of methanol and was passed to the middle of a two-inch (5 cm) diameter distillation sieve tray column having 30 trays. A distillate fraction of hydrocarbons of predominantly four carbon atoms was obtained from the top of this column and was substantially free (less than 10 mole ppm or 5 weight ppm) of methanol and eminently suitable as feed for either an alkylation process or a polymerization process for production of high octane components for gasoline blending. The residue fraction withdrawn continuously from the bottom of the distillation column was a high octane component for gasoline blending and upon analyses by gas chromatography was found to have the following composition:

| Component | Weight % |
|---|---|
| Unretractable $C_4$'s | 2.05 |
| Reactable $C_4$'s | 0.04 |
| Unreactable $C_5$'s | 51.14 |
| Reactable $C_5$'s | 14.86 |
| $C_6$ Hydrocarbons | 6.70 |
| Methanol | 0.0005 |
| M.T.B.E. | 12.90 |
| T.A.M.E. | 12.30 |

The proportions of reactable $C_4$ and $C_5$ hydrocarbons in the original feed stream that were converted to ethers and recovered in this blending component were 70% and 32% respectively in this single pass reaction. The ethylene glycol extract withdrawn from the bottom of the extraction column was found to contain 7.8% methanol and was fed to a packed stripping column in which the methanol was stripped from the glycol and recycled to the etherification reactor; stripped ethylene glycol containing 150 ppm methanol was recycled from the bottom of the stripping column to the top of the extraction column for further extraction of methanol.

EXAMPLE 2

An olefinic mixed hydrocarbon stream of origin similar to that of the hydrocarbon mixture used as feed in the previous example was used as raw material in this example and had the following proximate composition: 45.8% $C_4$ hydrocarbons, including 7.9% isobutylene and 37.9% $C_4$ hydrocarbons unreactable for MTBE production, 48.8% $C_5$ hydrocarbons including 16.6% isoamylenes and 32.2% $C_5$ hydrocarbons unreactable to form TAME, and 5.5% $C_6$ hydrocarbons (considered unreactable). Utilizing the apparatus used in Example 1 and additionally a 25-plate sieve tray fractional distillation column two inches in diameter, with its associated condenser and reboiler, the apparatus was arranged as shown diagrammatically in the accompanying drawing with the additional column used for fractionation of a recycle stream. The olefinic hydrocarbon stream was fed continuously to the reactor together with a recycle portion obtained as a distillate from the top of the foregoing additional sieve tray column; the recycle stream is further identified later herein. Simultaneously a stream of methanol was fed to the reactor in a molar ratio of 0.91 relative to the reactable $C_4$ and $C_5$ hydrocarbons in the total reactor feed. The total reactor feed rate produced an LHSV of 2.0 in the reactor, and the average temperature across the reactor was 180° F. (82° C.). Pressure in the reactor was maintained around 13.6 atmospheres. Effluent from the etherification reactor was extracted by a counter-current stream of ethylene glycol in the same manner as in Example 1, and the raffinate distilled as in Example 1, to provide a distillate of mixed predominantly $C_4$ hydrocarbons substantially free of methanol (less than 10 mole ppm) and suitable as feed for high octane alkylate or polygas production. A proportion of 30% of the residue from this first distillation was passed to the additional distillation column referred to above, wherein it was fractionated to provide a hydrocarbon distillate of predominantly five carbon atom hydrocarbons and a high octane residue containing MTBE and TAME formed in the reactor, along with the less volatile of the $C_5$ hydrocarbons and any higher boiling hydrocarbons in the feed. The remaining 70% of the residue from the first distillation was a high octane blending component suitable for blending directly into a gasoline pool. Fractionation in this additional distillation column was controlled to remove, in the distillate, most of the etherifiable $C_5$ hydrocarbons (isoamylenes) fed into the column from the preceding distillation. This distillate, which contained 1.76% $C_4$ hydrocarbons, 97.23% $C_5$ hydrocarbons including 21.70% isoamylenes, 1.53% $C_6$ hydrocarbons, and trace methanol, was recycled to the reactor as the recycle portion, referred to above, from the additional distillation column. The distillation residue, withdrawn from the bottom of the column, contained 35.45% MTBE, 36.48% TAME, trace methanol, balance $C_5$ and $C_6$ hydrocarbons including only 2.54% etherifiable $C_5$ hydrocarbons (isoamylenes), and was eminently suitable as a high octane blending component for blending into gasoline. The overall conversion to TAME of isoamylenes in the fresh feed, with the additional processing of 30% of the residue from the first distillation as thus described, was substantially 45%. A proportion of substantially 71% of the isobutylene in the fresh feed was converted to MTBE at the same time, with no recycle of any significant proportion of $C_4$ hydrocarbons from the raffinate.

Numerous advantages over the prior art are achieved by use of the present invention. The known method of removing unreacted methanol from etherification effluent by water washing requires preliminary distillation to separate and recover the ethers, which have significant solubility in water and could, to a considerable and unacceptable extent, be lost in the wash water. In the process of the present invention the volatility of the glycols, relative to the other components, and the miscibility of the glycols with $C_4$ and $C_5$ hydrocarbons are both sufficiently low that there is no significant risk of glycol entrainment or contamination in the predominantly hydrocarbon streams. Thus there need be no concern about glycol contamination of the $C_4$ hydrocarbon stream from the process when it is to be used in an alkylation unit or a polygas unit. Additionally, with respect to any miscibility of ethers in the glycol layer which, subsequent to contacting etherification effluent, normally is recovered by distillation of methanol therefrom, there is no tendency of the glycol to distill azeotropically with any traces of ethers therein because the glycol/ether pairs do not form azeotropes as the water/ether pairs generally do. Hence the more volatile ether can fractionally distill from the glycol along with methanol for recycle to an etherification unit and avoid causing any yield loss. Furthermore, the presence of glycol in an etherification step is not detrimental to the operation of that process, whereas the presence of any water which might be entrained in methanol being recycled to an etherification step would be detrimental to the etherification reactor operation. The low tolerance for water in hydrocarbon feed streams for HF alkylation processes generally requires that such feed streams be dried, e.g. with molecular sieves, and a preliminary water washing of such a feed stream would obviously require a subsequent drying step before HF alkylation. The use of glycol in the present invention precludes any need for drying HF alkylation feed streams with molecular sieves. Risk of corrosion by wet HF in such alkylations also is reduced by use of glycol in accordance with the present invention.

It will be recognized that numerous modifications may be incorporated within the process just described without departing from the spirit or scope of the invention, which is defined in the following claims.

We claim:

1. A method for processing an olefinic hydrocarbon stream consisting essentially of a mixture including both four and five carbon atom etherifiable olefins, for the formation of high octane components for blending into gasoline, said method comprising
    a. passing said stream into an etherification reactor with a proportion of methanol under etherifying conditions, to contact an etherification catalyst therein and etherify tertiary olefins in said stream,
    b. passing the entire effluent stream from said etherification reactor into a glycol contacting unit and contacting it therein with a stream of liquid glycol to remove methanol from said effluent and reduce the methanol concentration in the effluent stream to no greater than 200 mole ppm in said effluent,
    c. separating said effluent stream from said glycol and fractionally distilling the reduced effluent to separate a distillate containing hydrocarbons of predominantly four carbon atoms each and no greater than 200 mole ppm methanol from a higher boiling high octane fraction containing ethers and hydrocarbons of predominantly more than four carbon atoms each.

2. A method as claimed in claim 1 including the additional step of fractionally distilling a proportion of said higher boiling fraction to separate a distillate of hydrocarbons of predominantly five carbon atoms each from a higher boiling ether containing portion, and recycling said distillate of hydrocarbons of predominantly five carbon atoms each as additional feed to said etherification reactor.

3. A method as claimed in claim 1 and including the additional steps of fractionally distilling the glycol separated from the effluent stream to obtain a distillate of methanol and a residue of glycol, recycling said distillate of methanol as part of the methanol feed to said etherification reactor and recycling said residue of glycol to said glycol contacting unit as the stream of liquid glycol.

4. A method as claimed in claim 1, in which the glycol contacting unit is a counter-current liquid-liquid extractor.

5. A method as claimed in claim 1, in which the glycol is ethylene glycol.

6. A method as claimed in claim 1 in which the glycol is ethylene glycol which contacts the effluent in a mole ratio of glycol to effluent in the range from 0.1 to 4.0.

7. A method as claimed in claim 6 in which the mole ratio is in the range from 0.20 to 0.70.

8. A method as claimed in claim 2, in which the proportion of the said higher boiling fraction which is additionally fractionally distilled is a proportion in the range between 10% and 85% of said fraction.

9. A method as claimed in claim 8 in which the proportion is between 15% and 40%.

10. In a method of processing an olefinic hydrocarbon mixture including both four and five carbon atom etherifiable hydrocarbons, for the formation of high octane components for blending into gasoline, in which the mixture is reacted with methanol under etherifying conditions to etherify tertiary olefins therein and unreacted hydrocarbons of four carbon atoms are distilled from the etherified mixture for subsequent catalytic processing, the improvement which consists in contacting the etherified mixture containing unreacted methanol with an immiscible liquid glycol phase to remove methanol from the etherified mixture and reduce the methanol concentration in the mixture to no greater than 200 mole ppm, and subsequently separating the glycol phase containing the removed methanol from the etherified mixture before unreacted hydrocarbons of four carbon atoms are distilled from the etherified mixture.

* * * * *